United States Patent

Aya et al.

[11] 3,996,039
[45] Dec. 7, 1976

[54] SYNERGISTIC HERBICIDAL COMPOSITIONS

[75] Inventors: Masahiro Aya; Nubuo Fukazawa; Itsuro Kobori, all of Tokyo, Japan

[73] Assignee: Bayer Aktiengesellschaft, Leverkusen, Germany

[22] Filed: Aug. 6, 1974

[21] Appl. No.: 495,174

[30] Foreign Application Priority Data

Aug. 13, 1973 Japan .............................. 48-89986

[52] U.S. Cl. ........................................ 71/87; 71/90
[51] Int. Cl.² ........................................ A01N 9/36
[58] Field of Search ................................ 71/87, 90

[56] References Cited

UNITED STATES PATENTS

| | | | |
|---|---|---|---|
| 2,756,135 | 7/1956 | Searle | 71/90 |
| 3,740,209 | 6/1973 | Schrader et al. | 71/87 |
| 3,760,044 | 9/1973 | Schrader et al. | 71/87 |
| 3,787,538 | 1/1974 | Schrader et al. | 71/87 |
| 3,819,754 | 6/1974 | Aya et al. | 71/87 |
| 3,823,004 | 7/1974 | Schrader et al. | 71/87 |
| 3,845,069 | 10/1974 | Schafer et al. | 71/90 |

*Primary Examiner*—Glennon H. Hollrah
*Attorney, Agent, or Firm*—Burgess, Dinklage & Sprung

[57] ABSTRACT

Herbicidal compositions comprising as active ingredients
1. an amidothionophosphoric acid ester derivative of the general formula

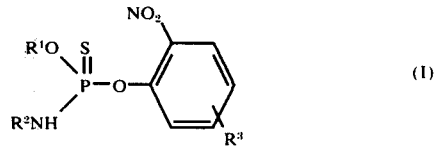

wherein
$R^1$ and $R^2$ are alkyl of from 1 to 6, preferably 1 to 4, carbon atoms,
$R^3$ is hydrogen or alkyl of from 1 to 6, preferably 1 to 4, carbon atoms and 2. a urea derivative of the formula

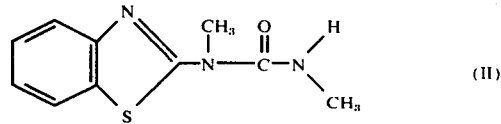

alone or in admixture with a solid or liquid or liquefied gaseous diluent or carrier; are outstandingly effective as herbicides and display synergistic potency.

15 Claims, No Drawings

SYNERGISTIC HERBICIDAL COMPOSITIONS

The present invention relates to new herbicidal compositions, particularly to synergistic combinations comprising certain amidothionophosphoric acid ester compounds and a certain urea compound.

The invention provides a herbicidal composition containing as active ingredients 1. an amidothionophosphoric acid ester derivative of the general formula

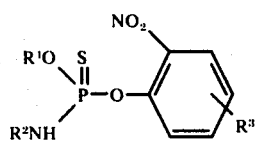

wherein $R^1$ and $R^2$ are alkyl of from 1 to 6, preferably 1 to 4, carbon atoms, $R^3$ is hydrogen or alkyl of from 1 to 6, preferably 1 to 4, carbon atoms and 2. a urea derivative of the formula

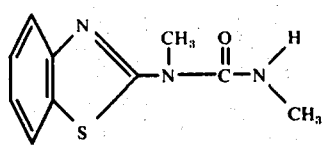

alone or in admixture with a solid or liquid or liquefied gaseous diluent or carrier.

The amidothionophosphoric acid ester type compound of the foregoing formula (I) is a germination and growth inhibiting type of herbicide, which is effective against field weeds before their germination.

While its effect as a stem and leaf treating agent is not very good, it is effective against such important annual and broad-leaved weeds as barnyard grass (*Digitaria ciliaris*), purslane and goosefoot, without having injurious effects on such crops as rice, wheat and vegetables, when used on fields as a pregermination soil treating agent at the rate of 200 – 300 grams per 10 ares. However, in the practical control of field weeds, it lacks effectiveness in controlling the weeds of the families *Polygonaceae* and *Graminaea*, with the consequence that it was necessary to apply far greater quantities for controlling both.

On the other hand, the urea derivative of formula (II), which is already known from U.S. Pat. No. 2,756,135, is a herbicide of the absorption and translocating type. This compound has the action of either inhibiting germination or causing the weeds to wither by impeding the photosynthesis reaction. This compound is usually applied at the rate of 200 to 300 grams per 10 ares, and while it possesses a relatively broad herbicidal spectrum with respect to the broadleaved field weeds, its effectiveness in controlling plants that are in the growing stage is poor, and especially it has the shortcoming that its effectiveness in controlling gramineous weeds is low. It has been used hitherto as a nonselective herbicide and in large amounts in an effort to effect the difficult control of gramineous seeds between germination and the 2 to 3-leaf stage, and can therefore injure crops. Moreover, since the duration of the effectiveness of this type of compound may extend over a long time, the growth of crops may be impeded by the remaining active compound. Hence, consideration must be given to crops that are to be planted subsequently, and care must be exercised in the application of this type of compound.

Our attempts to develop a herbicide not having the above shortcomings have eventually shown that when a composition having as its effective ingredient a mixture consisting of the foregoing compounds of formula (I) and (II), especially when mixed at a ratio of 0.5 – 5 parts by weight of the former to 1.0 parts by weight of the latter, was used for controlling weeds, a very conspicuous synergistic and cooperative weed controlling effect was obtained, even when the amounts of the two components were quite small, without causing any injury to crops, as compared with the case where each was used independently. In addition, even in the case of weeds at the 2 – 3-leaf stage (where the herbicidal activity was poor when each compound was used independently) there was manifested a cooperative and synergistic action between the two constituents of the mixture, and an excellent herbicidal activity was obtained.

While the urea compounds of formula (II) have excellent herbicidal activity, they have the serious disadvantage of causing phytotoxicity in crops. Thus, care has had in the past to be exercised as to the period, temperature and concentration at which they were applied. However, this problem has been solved by the present invention, and the ingredients can be used with safety since it is possible to use them in relatively small amounts.

While the mixed herbicide of the invention is especially effective as a soil treating agent, it can also be used as a stem and leaf treating agent. And since certain and lasting herbicidal effects are obtained against both gramineous and broad-leaved weeds, this herbicide is helpful in saving time and labor in farming.

The mixed herbicide of the invention can be applied in amounts of 50 – 200 grams per 10 ares (in the case of the compound of formula (I)) and of 50 – 200 grams per 10 ares (in the case of the compound of formula (II)), and this is very desirable from the standpoint of agricultural economy.

Examples of alkyl groups $R^1$, $R^2$ and $R^3$ include methyl, ethyl, n- or iso-propyl, and n-, iso-, sec.- or tert.-butyl.

Examples of the compounds of formula (I) are listed in Table 1.

Table 1

| Compound of formula (1) | Structural formula | Physical constants |
|---|---|---|
| 1-A | CH₃O, S, P(=S?)—O—C₆H₃(NO₂)(CH₃), iso-C₃H₇NH | m.p. 55–56° C. |
| 1-B | C₂H₅O, S, P—O—C₆H₃(NO₂)(CH₃), sec-C₄H₉NH | $n_D^{20}$ 1.5402 |
| 1-C | C₂H₅O, S, P—O—C₆H₃(NO₂)(CH₃), sec-C₄H₉NH | $n_D^{20}$ 1.5382 |
| 1-D | CH₃O, S, P—O—C₆H₄(NO₂), sec-C₄H₉NH | $n_D^{20}$ 1.5402 |

The mixture of active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents, and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

By liquefied gaseous diluents or carriers are meant liquids which would be gaseous at normal temperatures and pressures, e.g. aerosol propellants, such as halogenated hydrocarbons, e.g. freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin, sulfite waste liquors and methyl cellulose.

The mixture of compounds of the present invention can be used together with other agricultural chemicals, for example insecticides, fungicides, miticides, nematocides, antiviral agents, other herbicides, plant growth regulators, fertilizers, and attractants; including for example organic phosphoric ester type compounds, carbamate type compounds, dithio (or thiol) carbamate type compounds, organic chlorine type compounds, dinitro type compounds, organic sulfur or metal type compounds, antibiotics, substituted diphenyl ether type compounds, urea type compounds and triazine type compounds.

The active compound mixture can be used as such or in the form of its formulations or the use forms prepared therefrom, such as ready to use solutions, emulsifiable concentrates, emulsions, foams, suspensions, spraying powders, pastes, soluble powders, dusting agents and granules. They may be applied in customary manner, for example by squirting, spraying, atomizing, dusting, sprinkling, fumigating, gassing, watering, dressing or encrusting.

The formulations in general contain 0.1 – 95% by weight, and preferably 0.5 – 90% by weight, of total active ingredients.

They may be diluted for actual application, and the total active compound concentrations in the ready-to-use preparations may for example be 0.0001 – 20% by weight, and preferably 0.005 to 10% by weight.

The content of active ingredients can be suitably varied depending upon the form of the preparation, the method of its application, the purpose, the season, the place and the conditions of weed infestation.

The active compound mixture can be used in the ultra-low-volume (ULV) method, where it is possible to apply formulations of up to 95% strength or even 100% strength.

The active compound mixture is generally applied to an area of agriculture in an amount of 50 – 400 grams, preferably 150 – 350 grams, of total active ingredients per 10 ares. However, in special cases the rate of application may have to be either more or less than the foregoing range.

The invention also provides a method of combating weeds which comprises applying to the weeds or a weed habitat a composition according to the invention.

The invention also provides means of yielding crops protected from damage by weeds by being grown in areas in which, immediately prior to and/or during the time of the growing, a composition according to the invention was applied. It will be seen that the usual methods of providing a harvested crop may be improved by the present invention.

The compositions according to the invention, and their use according to the invention, are illustrated by the following Examples.

EXAMPLE 1

(Wettable powder)

Ten parts of the active ingredient (I-A), 10 parts of the active ingredient (II), 78 parts of a 1:5 mixture of diatomaceous earth and kaolin, and 2 parts of the emulsifier RUNOX (polyoxyethylene alkylaryl ether) were comminuted and mixed to prepare a wettable powder. This powder was diluted with water, and weeds and areas infested with weeds were treated by being sprayed with this aqueous composition.

EXAMPLE 2

(Emulsifiable concentrate)

Fifteen parts of the active ingredient (I-B), 15 parts of the active ingredient (II), 35 parts of xylene, 15 parts of KAWAKASOL (methylnaphthalene) and 20 parts of SOLPOL (polyoxyethylene alkylaryl ether) were mixed with stirring to prepare an emulsion. This emulsifiable concentrate was diluted with water, and weeds and areas infested with weeds were treated by being sprayed with this emulsion.

EXAMPLE 3

(Dust)

Two parts of the active compound (I-C), 1.0 part of the active compound (II) and 97 parts of a 1:3 mixture of talc and clay were comminuted and mixed to prepare a dust. Weeds and weed-infested areas were dusted with the preparation.

EXAMPLE 4

(Granular preparation)

To a mixture of 2.5 parts of the active compound (I-D), 2.5 parts of the active compound (II), 10 parts of bentonite, 83 parts of a 1:3 mixture of talc and clay, and 2 parts of lignin sulfite was added 25 parts of water, followed by thorough kneading of the mixture. This mixture was then cut into fine pieces with an extruding granulator to obtain granules of 20 – 40-mesh size, which were dried at 40° – 50° C to prepare a granular preparation. This preparation was dispersed over weeds and weed-infested areas.

The unexpectedly excellent performance and effectiveness of the herbicides of the present invention are illustrated by the following tests in which the herbicides of the invention were used against various weeds.

EXAMPLE A

Preparation of active compound for use in treatment tests of soils planted with field weeds and various crops.

Carrier: Five parts by weight of acetone

Emulsifier: One part by weight of benzyloxypolyglycol ether.

The preparation of the active compounds was obtained as an emulsifiable concentrate by mixing one part by weight of the active compound mixture with the foregoing carrier and emulsifier in the amounts indicated. The prescribed concentrate in which the chemical was to be used was obtained by diluting the foregoing preparation with water.

Test method

After filling a vessel 20 centimeters in width, 30 centimeters in length and 12 centimeters in depth with black volcanic ash soil, seeds of barnyard grass, *Digitaria ciliaris*, *Cyperus microiria*, *Amaranthus blitum*, *Polygonum blumei*, purslane, goosefoot, chickweed and kew-weed were seeded in rows and lightly covered with soil. Another vessel was seeded in similar manner with rice, wheat, maize, soy bean, peanut, carrot and radish seeds and covered lightly with soil. In each case one day after seeding and planting, the mixed preparation of the invention was used in the form of an emulsifiable concentrate to treat the surface of the soil by spraying it thereon at the rate of 10 milliliters per square meter after diluting the emulsifiable concentrate to the desired chemical concentration with water. Thirty days after the treatment with the chemical, the weed controlling effectiveness and phytotoxicity to the crops were evaluated on a scale of 0 – 5 shown below. The results obtained are shown in Table 2, the ratings being the average value of two replicates of the test.

The evaluation of the effectiveness, which was made by comparison with an untreated plot, was rated on the following scale:

| | | |
|---|---|---|
| 5: | A herbicidal effectiveness, when compared with the untreated plot, of above 95% (withering of weeds) | |
| 4: | " | above 80% |
| 3: | " | above 50% |
| 2: | " | above 20% |
| 1: | " | less than 20% |
| 0: | " | 0% (no effect) |

The evaluation of the phytotoxicity to the crops, which was made by comparison with an untreated plot, was rated on the following scale:

| | | |
|---|---|---|
| 5: | Phytotoxicity effect, when compared with the untreated plot, of above 95% (either the plants die completely or germination does not occur) | |
| 4: | " | above 80% (fatal injury) |
| 3: | " | above 50% (conspicuous injury) |
| 2: | " | above 20% (considerable injury or retardation of growth) |
| 1: | " | less than 20% (slight injury or slight retardation of growth) |
| 0: | " | 0% (no phytotoxicity) |

Table 2

| | | | Soil treatment test results relative to field weeds and various crops | | | | | | | |
|---|---|---|---|---|---|---|---|---|---|---|
| Compound mixture | Amount of compound of formula (I) (g/10 ares) | Amount of compound of formula (II) (g/10 ares) | Phytotoxicity | | | | | | | |
| | | | Rice | Wheat | Corn | Soy Bean | Peanut | Carrot | Radish | |
| I-A + II | 150 | 200 | 2 | 0 | 0 | 0 | 0 | 2 | 3 | |
| | 100 | 100 | 0 | 0 | 0 | 0 | 0 | 1 | 1 | |
| | 50 | 50 | 0 | 0 | 0 | 0 | 0 | 0 | 0 | |
| | 150 | 100 | 0 | 0 | 0 | 0 | 0 | 1 | 1 | |
| | 75 | 50 | 0 | 0 | 0 | 0 | 0 | 0 | 0 | |
| | 100 | 50 | 0 | 0 | 0 | 0 | 0 | 0 | 0 | |
| I-B + II | 150 | 200 | 2 | 0 | 0 | 0 | 0 | 2 | 2 | |
| | 100 | 100 | 1 | 0 | 0 | 0 | 0 | 0 | 1 | |
| | 50 | 50 | 0 | 0 | 0 | 0 | 0 | 0 | 0 | |
| | 150 | 100 | 1 | 0 | 0 | 0 | 0 | 1 | 1 | |
| | 75 | 50 | 0 | 0 | 0 | 0 | 0 | 0 | 0 | |
| | 100 | 50 | 0 | 0 | 0 | 0 | 0 | 0 | 0 | |
| I-C + II | 150 | 200 | 2 | 1 | 0 | 0 | 1 | 2 | 2 | |
| | 100 | 100 | 1 | 0 | 0 | 0 | 0 | 1 | 1 | |
| | 50 | 50 | 0 | 0 | 0 | 0 | 0 | 0 | 0 | |
| | 150 | 100 | 1 | 0 | 0 | 0 | 0 | 2 | 2 | |
| | 75 | 50 | 0 | 0 | 0 | 0 | 0 | 0 | 0 | |
| | 100 | 50 | 0 | 0 | 0 | 0 | 0 | 0 | 0 | |
| I-D + II | 150 | 200 | 2 | 0 | 0 | 0 | 0 | 2 | 2 | |
| | 100 | 100 | 1 | 0 | 0 | 0 | 0 | 0 | 1 | |
| | 50 | 50 | 0 | 0 | 0 | 0 | 0 | 0 | 0 | |
| | 150 | 100 | 1 | 0 | 0 | 0 | 0 | 1 | 1 | |
| | 75 | 50 | 0 | 0 | 0 | 0 | 0 | 0 | 0 | |
| | 100 | 50 | 0 | 0 | 0 | 0 | 0 | 0 | 0 | |
| I-A | 150 | — | 0 | 0 | 0 | 0 | 0 | 0 | 0 | |
| | 100 | — | | | | | | | | |
| | 75 | — | | | | | | | | |
| | 50 | — | | | | | | | | |
| I-B | 150 | — | 0 | 0 | 0 | 0 | 0 | 0 | 0 | |
| | 100 | — | | | | | | | | |
| | 75 | — | | | | | | | | |
| | 50 | — | | | | | | | | |
| I-C | 150 | — | 0 | 0 | 0 | 0 | 0 | 0 | 0 | |
| | 100 | — | | | | | | | | |
| | 75 | — | | | | | | | | |
| | 50 | — | | | | | | | | |
| I-D | 150 | — | 0 | 0 | 0 | 0 | 0 | 0 | 0 | |
| | 100 | — | | | | | | | | |
| | 75 | — | | | | | | | | |
| | 50 | — | | | | | | | | |
| II | — | 200 | 2 | 0 | 0 | 0 | 0 | 2 | 3 | |
| | — | 100 | 0 | 0 | 0 | 0 | 0 | 1 | 1 | |
| | — | 50 | 0 | 0 | 0 | 0 | 0 | 0 | 0 | |

| Compound mixture | Amount of compound of formula (I) (g/10 ares) | Amount of compound of formula (II) (g/10 ares) | Effectiveness | | | | | | | | |
|---|---|---|---|---|---|---|---|---|---|---|---|
| | | | Barnyard grass | Digitaria ciliaris | Cyperus microiria | Amaranthus blitumn | Polygonum blumei | purslane | Goosefoot | Chickweed | Kewweed |
| I-A + II | 150 | 200 | 5 | 5 | 5 | 5 | 5 | 5 | 5 | 5 | 5 |
| | 100 | 100 | 5 | 5 | 5 | 5 | 5 | 5 | 5 | 5 | 5 |
| | 50 | 50 | 4–5 | 4–5 | 4–5 | 4–5 | 5 | 5 | 5 | 5 | 4–5 |
| | 150 | 100 | 5 | 5 | 5 | 5 | 5 | 5 | 5 | 5 | 5 |
| | 75 | 50 | 4–5 | 5 | 5 | 4–5 | 5 | 5 | 5 | 5 | 4–5 |
| | 100 | 50 | 5 | 5 | 5 | 5 | 5 | 5 | 5 | 5 | 4–5 |
| I-B + II | 150 | 200 | 5 | 5 | 5 | 5 | 5 | 5 | 5 | 5 | 5 |
| | 100 | 100 | 5 | 5 | 5 | 5 | 5 | 5 | 5 | 5 | 5 |
| | 50 | 50 | 4 | 4 | 4 | 5 | 4–5 | 4–5 | 5 | 5 | 4–5 |
| | 150 | 100 | 5 | 5 | 5 | 5 | 5 | 5 | 5 | 5 | 5 |
| | 75 | 50 | 4 | 4–5 | 4–5 | 5 | 5 | 5 | 5 | 5 | 4–5 |
| | 100 | 50 | 5 | 5 | 5 | 5 | 5 | 5 | 5 | 5 | 4–5 |
| I-C + II | 150 | 200 | 5 | 5 | 5 | 5 | 5 | 5 | 5 | 5 | 5 |
| | 100 | 100 | 5 | 5 | 5 | 5 | 5 | 5 | 5 | 5 | 5 |
| | 50 | 50 | 4 | 4 | 4 | 4–5 | 5 | 5 | 5 | 5 | 4–5 |
| | 150 | 100 | 5 | 5 | 5 | 5 | 5 | 5 | 5 | 5 | 5 |
| | 75 | 50 | 5 | 5 | 5 | 5 | 5 | 5 | 5 | 5 | 4–5 |
| | 100 | 50 | 4–5 | 5 | 5 | 5 | 5 | 5 | 5 | 5 | 4–5 |
| I-D + II | 150 | 200 | 5 | 5 | 5 | 5 | 5 | 5 | 5 | 5 | 5 |
| | 100 | 100 | 5 | 5 | 5 | 5 | 5 | 5 | 5 | 5 | 5 |
| | 50 | 50 | 3–4 | 3–4 | 3–4 | 4–5 | 5 | 5 | 5 | 5 | 4 |
| | 150 | 100 | 5 | 5 | 5 | 5 | 5 | 5 | 5 | 5 | 5 |
| | 75 | 50 | 4 | 4 | 4 | 5 | 5 | 5 | 5 | 5 | 4–5 |
| | 100 | 50 | 4–5 | 4–5 | 4–5 | 5 | 5 | 5 | 5 | 5 | 4–5 |
| I-A | 150 | — | 4 | 4 | 4 | 4 | 3 | 4 | 4 | 4 | 2 |
| | 100 | — | 3–4 | 3–4 | 3 | 3 | 0 | 3 | 3 | 3 | 0 |
| | 75 | — | 3 | 3 | 3 | 3 | | 3 | 3 | 3 | |
| | 50 | — | 3 | 3 | 2 | 2 | | 2 | 2 | 2 | |
| I-B | 150 | — | 4 | 4 | 4 | 4 | 3 | 4 | 3 | 4 | 2 |
| | 100 | — | 3–4 | 3–4 | 3 | 3 | 0 | 3 | 3 | 3 | 0 |
| | 75 | — | 3 | 3 | 3 | 3 | | 3 | 2–3 | 3 | |
| | 50 | — | 3 | 3 | 2 | 2 | | 2 | 2 | 2 | |
| I-C | 150 | — | 4 | 4 | 4 | 4 | 3 | 4 | 4 | 4 | 3 |
| | 100 | — | 3–4 | 3–4 | 3 | 3 | 0 | 3 | 2–3 | 3 | 0 |
| | 75 | — | 3 | 3 | 3 | 3 | | 3 | 2 | 3 | |
| | 50 | — | 3 | 3 | 2 | 2 | | 2 | 1 | 2 | |

Table 2-continued

|  |  |  |  |  |  |  |  |  |  |  |  |
|---|---|---|---|---|---|---|---|---|---|---|---|
|  | 150 | — | 4 | 4 | 4 | 3–4 | 3 | 4 | 3 | 4 | 1 |
|  | 100 | — | 3–4 | 3–4 | 3 | 3 | 0 | 3 | 2 | 3 | 0 |
| I-D | 75 | — | 3 | 3 | 2 | 2 |  | 2 | 1–2 | 2 |  |
|  | 50 | — | 2 | 2 | 1 | 1 |  | 1 | 1 | 1 |  |
|  | — | 200 | 2 | 3 | 2 | 5 | 5 | 5 | 5 | 5 | 5 |
| II | — | 100 | 0 | 0 | 0 | 4 | 4 | 4 | 4 | 4 | 4 |
|  | — | 50 | 0 | 0 | 0 | 3–4 | 3–4 | 4 | 4 | 4 | 3–4 |

EXAMPLE B

Stem and leaf treatment test relative to field weeds and onion.

Test method

A vessel 30 centimeters in length, 20 centimeters in width and 12 centimeters in depth was filled with black volcanic ash soil, after which the seeds of the weeds barnyard grass, *Digitaria ciliaris*, *Cyperus microiria*, *Amaranthus blitum*, *Polygonum blumei*, purslane, goosefoot, chickweed and kew-weed, were seeded in rows and lightly covered with soil. In the same vessel were also transplanted onion plants of the 3-leaf stage.

When the stem height of the seeded weeds reached 4–7 centimeters (about 15 days after planting), the mixed preparation of the invention was used as in Example A in the form of an emulsifiable concentrate to treat the plants by spraying the emulsion onto the leaves of the plants at the rate of 100 milliliters per square meter after diluting it to the desired concentration with water. Thirty days after the treatment with the chemical, the weed controlling effectiveness and the selectivity with respect to onion were investigated in accordance with the same criteria as in Example A, the ratings being the average value of two replicates of the test.

The results obtained are shown in Table 3.

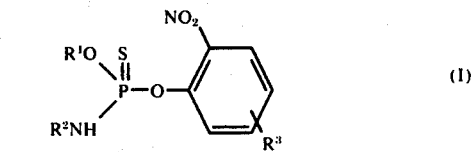

wherein
  $R^1$ and $R^2$ are alkyl of from 1 to 6 carbon atoms; and
  $R^3$ is hydrogen or alkyl of from 1 to 6 carbon atoms; and
2. a urea derivative of the formula

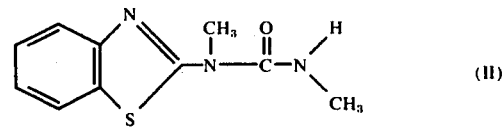

and an inert diluent, the compound I being present in a relative amount to compound II such that the weight ratio of compound I to compound II is 1-2:1.

2. Herbicidal composition as claimed in claim 1 wherein $R^1$ and $R^2$ in formula (I) are individually selected from alkyl of from 1 to 4 carbon atoms.

3. Herbicidal composition as claimed in claim 1 wherein $R^3$ in formula (I) is hydrogen.

4. Herbicidal composition as claimed in claim 1 wherein $R^3$ in formula (I) is alkyl of from 1 to 4 carbon atoms.

5. Herbicidal composition as claimed in claim 1 wherein said amidothionophosphoric acid ester compound (1) is of the formula

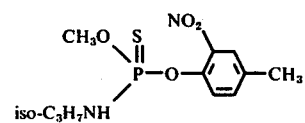

Table 3

Results of stem and leaf treatment test relative to field weeds and onion

| Compound | Amount of compound of formula (I) (g/10 ares) | Amount of compound of formula (II) (g/10 ares) | Effectiveness | | | | | | | | | Photo-toxicity |
|---|---|---|---|---|---|---|---|---|---|---|---|---|
|  |  |  | Barn-yard grass | Digi-taria cili-aris | Cyper-us micro-iria | Amar-anthus blitum | Poly-gonum blumei | Purs-lane | Goose foot | Chick-weed | Kew-weed | Onion |
| I-A | 250 | 100 | 5 | 5 | 5 | 5 | 5 | 5 | 5 | 5 | 5 | 0 |
| + | 200 | 75 | 5 | 5 | 5 | 5 | 5 | 5 | 5 | 5 | 5 | 0 |
| II | 150 | 50 | 4–5 | 4 | 5 | 5 | 5 | 5 | 5 | 5 | 5 | 0 |
|  | 250 | — | 2 | 2 | 0 | 0 | 0 | 0 | 0 | 0 | 0 | 0 |
| I-A | 200 | — | 0 | 0 |  |  |  |  |  |  |  |  |
|  | — | 100 | 2 | 3 | 3 | 4–5 | 5 | 5 | 5 | 5 | 5 | 0 |
| II | — | 75 | 1 | 2 | 2 | 4 | 4 | 4–5 | 5 | 4 | 4 |  |
|  | — | 50 | 1 | 1 | 1 | 3 | 3 | 4 | 4–5 | 4 | 4 |  |

It will be appreciated that the instant specification and examples are set forth by way of illustration and not limitation, and that various modifications and changes may be made without departing from the spirit and scope of the present invention.

What is claimed is:

1. Herbicidal composition consisting essentially of as active ingredients effective amounts of
   1. an amidothionophosphoric acid ester compound of the formula 6. Herbicidal composition as claimed in claim 1 wherein said amidothionophosphoric acid ester compound (1) is of the formula

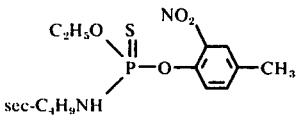

7. Herbicidal composition as claimed in claim 1 wherein said amidothionophosphoric acid ester compound (1) is of the formula

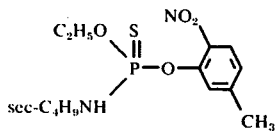

8. Herbicidal composition as claimed in claim 1 wherein said amidothionophosphoric acid ester compound (1) is of the formula

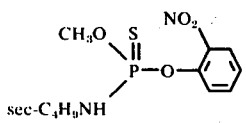

9. Herbicidal composition as claimed in claim 1 wherein said inert diluent is a carrier selected from the group consisting of solid, liquid and liquefied gaseous carriers.

10. Herbicidal composition as claimed in claim 1 wherein said active ingredients comprise from 0.1 to 95% of the total active ingredients by weight.

11. Method of combating undesired vegetation, which method consists essentially of applying to the locus thereof an effective amount of a herbicidal composition consisting essentially of as active ingredients
1. an amidothionophosphoric acid ester compound of the formula

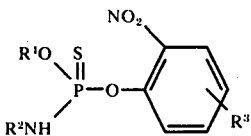

(I)

wherein
R¹ and R² are alkyl of from 1 to 6 carbon atoms; and
R³ is hydrogen or alkyl of from 1 to 6 carbon atoms; and 2. a urea derivative of the formula

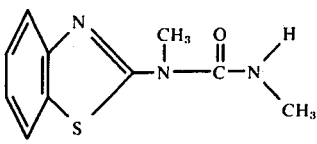

(II)

the compound I being present in said herbicidal composition in a relative amount to compound II such that the weight ratio of compound I to compound II is 1-2:1.

12. Method as claimed in claim 11 wherein said amidothionophosphoric acid ester compound is of the formula

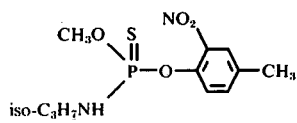

13. Method as claimed in claim 11 wherein said amidothionophosphoric acid ester compound is of the formula

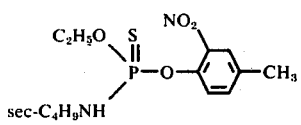

14. Method as claimed in claim 11 wherein said amidothionophosphoric acid ester compound is of the formula

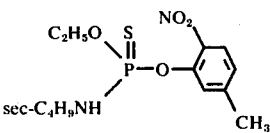

15. Method as claimed in claim 11 wherein said amidothionophosphoric acid ester compound is of the formula

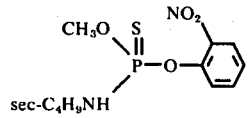

* * * * *